(12) United States Patent
McGough et al.

(10) Patent No.: US 10,534,076 B2
(45) Date of Patent: Jan. 14, 2020

(54) SHEAR VISCOSITY IMAGING WITH ACOUSTIC RADIATION FORCE

(71) Applicants: Board of Trustees of Michigan State University, East Lansing, MI (US); Mayo Foundation for Medical Education and Research, Rochester, MN (US)

(72) Inventors: Robert J. McGough, Okemos, MI (US); Yiqun Yang, East Lansing, MI (US); Matthew W. Urban, Rochester, MN (US)

(73) Assignees: Board of Trustees of Michigan State University, East Lansing, MI (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/577,711

(22) PCT Filed: Jun. 22, 2016

(86) PCT No.: PCT/US2016/038704
§ 371 (c)(1),
(2) Date: Nov. 28, 2017

(87) PCT Pub. No.: WO2016/209922
PCT Pub. Date: Dec. 29, 2016

(65) Prior Publication Data
US 2018/0156902 A1   Jun. 7, 2018

Related U.S. Application Data

(60) Provisional application No. 62/182,931, filed on Jun. 22, 2015.

(51) Int. Cl.
*G01S 7/52* (2006.01)
*G01S 15/89* (2006.01)
(Continued)

(52) U.S. Cl.
CPC .......... *G01S 7/52042* (2013.01); *A61B 8/485* (2013.01); *G01N 11/00* (2013.01);
(Continued)

(58) Field of Classification Search
CPC ............. G01S 7/52042; G01S 7/52052; G01S 15/8915; A61B 8/485; G01N 11/00; G01N 2011/0073
See application file for complete search history.

(56) References Cited

U.S. PATENT DOCUMENTS

2014/0018679 A1   1/2014   Chen et al.
2014/0112544 A1   4/2014   Yu et al.
(Continued)

*Primary Examiner* — Matthew G Marini
(74) *Attorney, Agent, or Firm* — Quarles & Brady LLP

(57) ABSTRACT

Shear waves are generated and measured in viscoelastic phantoms by a single push beam. Using numerical simulations or an analytical function to describe the diffraction of the shear wave, the resulting shear wave motion induced by the applied push beam is calculated with different shear elasticity values and then convolved with a separate expression that describes the effects of viscosity value for the medium. The optimization algorithm chooses the tissue parameters which provide the smallest difference between the measured shear waveform and the simulated shear waveform. A shear viscosity image is generated by applying such optimization procedure at all of the observation points.

16 Claims, 13 Drawing Sheets

(51) Int. Cl.
*A61B 8/08* (2006.01)
*G01N 11/00* (2006.01)

(52) U.S. Cl.
CPC ...... *G01S 7/52052* (2013.01); *G01S 15/8915* (2013.01); *G01N 2011/0073* (2013.01)

(56) References Cited

U.S. PATENT DOCUMENTS

2015/0148675 A1 5/2015 Haupt
2015/0272547 A1 10/2015 Freiburger et al.

SHEAR VISCOSITY IMAGING WITH ACOUSTIC RADIATION FORCE

CROSS-REFERENCE TO RELATED APPLICATIONS

This application is a National Phase Entry of International Application Serial No. PCT/US2016/038704, filed on Jun. 22, 2016, which claims the benefit of U.S. Provisional Application No. 62/182,931 filed on Jun. 22, 2015. The entire disclosure of the above applications are incorporated herein by reference.

GOVERNMENT RIGHTS

This invention was made with government support under EB012079 and DK092255 awarded by the National Institutes of Health. The government has certain rights in this invention.

FIELD

The present disclosure relates to a method for determining shear viscosity and imaging of shear viscosity using ultrasound.

BACKGROUND

Shear wave elastography is a burgeoning technique which provides mechanical properties of soft human tissue through noninvasively diagnostic ultrasound testing. Its applications include diagnostics in breast, prostate, liver, kidney, thyroid, heart, and blood vessels. Several different methods have been developed for shear wave elastography, for example, shear wave elasticity imaging (SWEI). In SWEI, an acoustic radiation force (push) is applied to soft tissue for a short duration, and the transient shear wave displacement response in the tissue is measured using high framerate ultrasound. Other methods for shear wave elastography include acoustic radiation force imaging (ARFI), supersonic shear imaging (SSI), spatially modulated ultrasound radiation force (SMURF), crawling wave spectroscopy (CWS), and comb-push ultrasound shear elastography (CUSE).

Among the above introduced shear wave elastography methods, SWEI, SSI, SMURF, CWS, and CUSE are quantitative methods, which provide shear wave speed values of the tissue locally. Conventionally, the local shear wave speed is estimated using a time-of-flight algorithm based on a one-dimensional (1 D) correlation method. To estimate the shear elasticity of a spatial point, the time-of-flight estimation is obtained by applying a one-dimensional cross-correlation of the shear waveform measured at two spatial points located at both lateral sides of an estimation point. These two spatial points have the same depth as the estimation point, but have different lateral distances away from the push beam. The shear wave $c_s$ is calculated by dividing the distance between the two lateral points by the time of flight, then the shear elasticity value is obtained using $\mu = \rho c_s^2$, where $\rho$ is the density, and $\mu$ is the shear elasticity.

Although the time-of-flight method provides a useful estimate of the shear elasticity, it has some drawbacks, and there is significant room for improvement. First, the time-of-flight method inherently assumes the shear wave propagates as a plane wave. However, this assumption is not accurate as shear wave diffraction is not considered in this plane wave model. The shear waves are induced by the acoustic radiation force and are diffracted away from the source. Shear wave propagation is poorly described by simple plane wave propagation. Moreover, this method considers that the tissue is purely elastic and ignores the viscoelasticity of the tissue. This assumption is also not accurate as several studies have proved that the tissue is viscoelastic. These two inaccurate assumptions lead to inaccurate estimates of the shear elasticity value. Furthermore, the shear viscosity value of the tissue is another important tissue parameter that should be useful in diagnostic applications. It would be useful to develop a method to quantitatively estimate the shear viscosity value of soft tissue. So, based on the above backgrounds, the first motivation of this disclosure is to examine whether the time-of-flight method provides accurate parameter estimation in viscoelastic tissue, while the second motivation of the disclosure is to develop a method which provides more accurate estimates of the shear elasticity and shear viscosity values.

This section provides background information related to the present disclosure which is not necessarily prior art.

SUMMARY

This section provides a general summary of the disclosure, and is not a comprehensive disclosure of its full scope or all of its features.

A method is provided for determining the shear viscosity of an object, which is for example comprised of soft tissue. The method includes: applying an ultrasound wave to the object; measuring a shear wave waveform representing motion of a shear wave propagating through the object; estimating shear wave speed from the measured shear wave waveform; and generating a plurality of simulated shear wave waveforms in an elastic medium, where each simulated shear wave waveform in the plurality of simulated shear wave waveforms corresponds to a different shear speed in a range of shear speed values. To determine the shear viscosity, attenuation and dispersion effects of shear wave diffraction are modeled with a mathematical function, where the mathematical function includes a term indicative of shear viscosity; each of the simulated shear wave waveforms in the plurality of simulated shear wave waveforms are convolved with the mathematical function to yield a plurality of convolved shear displacement waveforms; and the shear viscosity for the object is estimated by minimizing the error between the measured shear wave waveform and the plurality of convolved shear displacement waveforms.

In some embodiments, shear speed can be estimated from the measured shear wave waveform using a k-space method. In some embodiments, the plurality of simulated shear wave waveforms are generated using Green's functions. In some embodiments, attenuation and dispersion effects of shear wave diffraction are modeled using a Gaussian function.

In one aspect of his disclosure, images of shear viscosity can be generated using the estimated shear viscosity and then displayed on a display of an ultrasound system. More specifically, the images of shear viscosity are generated by performing the steps of estimating shear wave speed, generating a plurality of simulated shear wave waveforms, convolving each of the simulated shear wave waveforms and estimating shear viscosity at different points in space within the object.

In another aspect of this disclosure, the above methods can be extended to improve upon the estimates for shear speed and/or shear viscosity. For example, a 1D optimization can be used to estimate shear wave speed (shear elasticity) and shear viscosity (shear attenuation and dispersion). In another example, shear wave speed and shear elasticity can be estimated simultaneously using a two-dimensional (2D) optimization.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 16A:
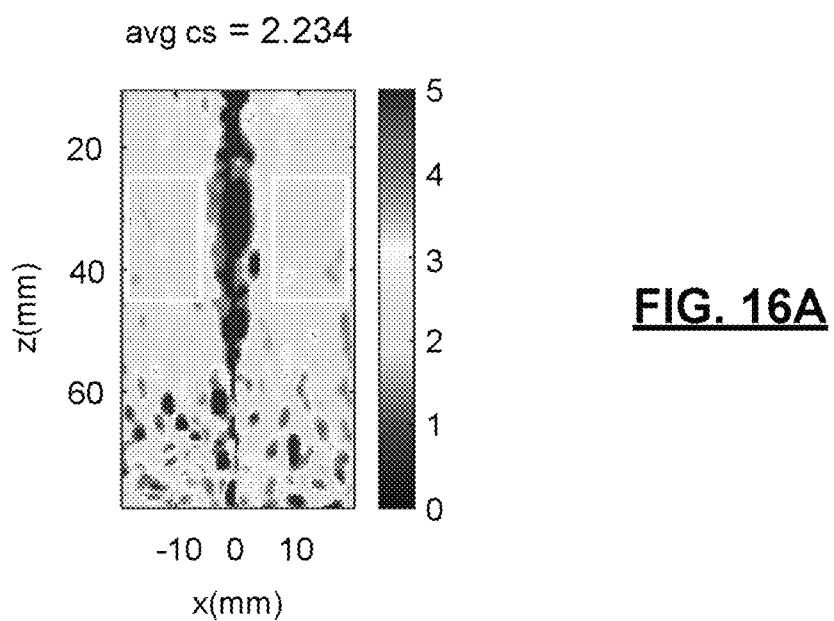
Figure 16B:
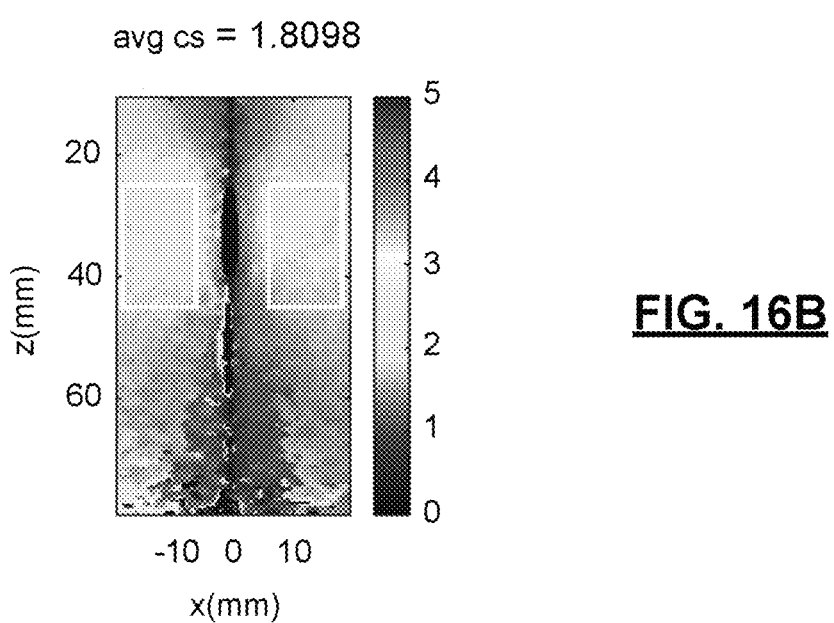
Figure 17:
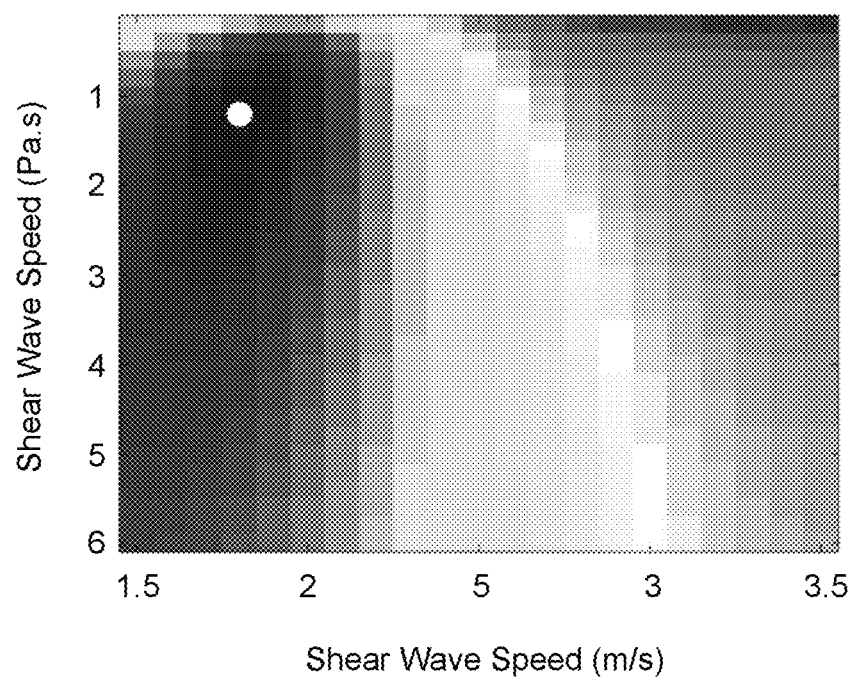

FIGS. 16A and 16B are an initial shear speed image obtained from steps 1-6 obtained from the same viscoelastic shear wave phantom described herein and a shear viscosity compensated image of the shear speed obtained from the same viscoelastic shear wave phantom using the method described herein, respectively; and FIG. 17 is a graph of the calculated error between the measured and simulated shear displacement waveforms plotted as a function of the shear speed and the shear viscosity at a particular point in space.

Corresponding reference numerals indicate corresponding parts throughout the several views of the drawings.

DETAILED DESCRIPTION

Example embodiments will now be described more fully with reference to the accompanying drawings.

In clinical ultrasound elastography, shear waves in the tissue are induced by an applied acoustic radiation force, which is generated by a focused ultrasound beam. The acoustic radiation force is modeled as $$f(r,t) = \frac{2\alpha I(r,t)}{c_p} \quad (1)$$

where f(r,t) is the body force where r denotes a spatial point in Cartesian coordinates and t denotes time, α is the attenuation coefficient, $c_p$ is the compressional wave speed, and I(r,t) is the acoustic intensity which is applied to the tissue. The intensity of the ultrasound beam is proportional to the square of the acoustic pressure defined as $I=p^2/\rho c_p$. In many shear wave elastography methods, the acoustic radiation force is applied to the tissue for a short period of time (~50-800 μs) to produce the shear wave. For example, the acoustic radiation force f(r,t) can be written as f(r,t)=f(r)w(t), where f(r) is the spatial distribution of the acoustic radiation force, and w(t) is the time window function describing the time dependence of the acoustic radiation force. The window function is given as w(t)=rec[(t−T/2)/T], where rect (•) is the rectangle or boxcar function, and T is the duration of the push. After the shear waveforms are generated, they are measured and processed to determine the characteristic mechanical properties of the tissue.

Figure 1:
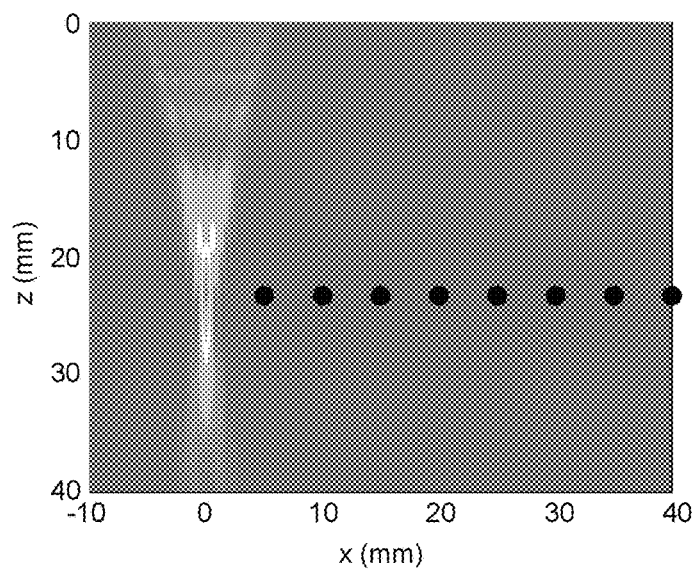
FIG. 1 is an image of a two-dimensional cross-section of a focused three-dimensional push beam.
Figure 2:
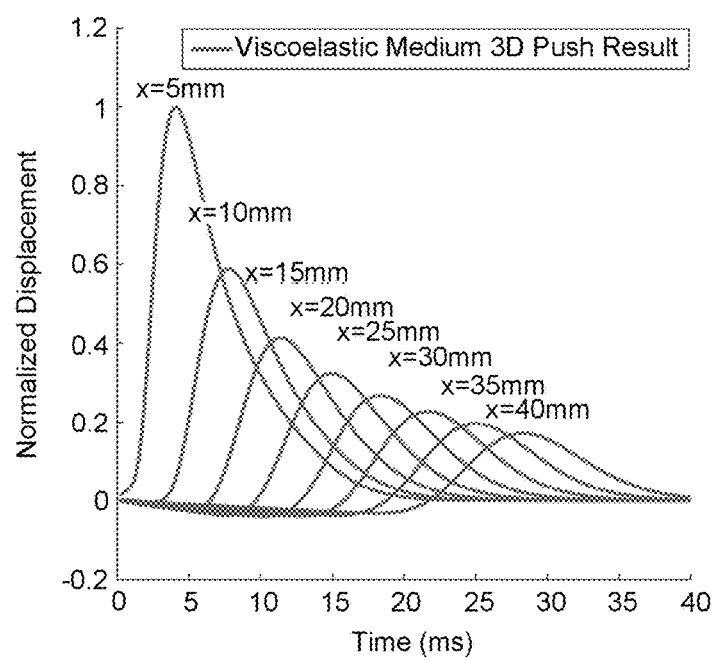
FIG. 2 is a graph depicting simulated shear displacement waveforms in a viscoelastic medium.
Figure 3:
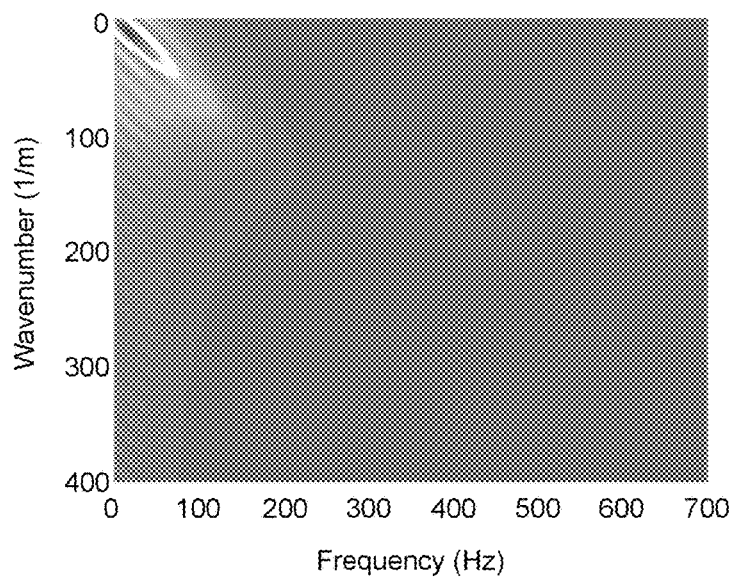
FIG. 3 is an image of a first quadrant of a k-space representation for FIG. 2.

The shear wave displacement u generated by an acoustic radiation force f in a visoelastic medium is modeled by Navier's equation with viscous loss as $$\left[\lambda + \mu + (\eta_p + \eta_s)\frac{\partial}{\partial_t}\right]\nabla\nabla\cdot u + \left(\mu + \eta_s\frac{\partial}{\partial_t}\right)\nabla^2 u + \rho f = \rho\ddot{u} \quad (2)$$

where λ and μ are the Lamé constants, $\eta_s$ and $\eta_p$ are the compressional and shear viscosities, respectively, ρ is the density, $c_p=\sqrt{(\lambda+2\mu)/\rho}$ and $c_s=\sqrt{\mu/\rho}$ are the compressional and shear speeds, respectively, u is the vector displacement, and f is the body force. The shear wave displacements, which are obtained from three-dimensional (3D) simulations of Equation 2 or from postprocessed ultrasound data, can then provide estimates of the shear elasticity μ with, for example, a k-space approach or a correlation-based approach. Examples of a simulated intensity field that generates the acoustic radiation force in a full 3D viscoelastic simulation, the corresponding shear wave displacements evaluated at the observation points, and the k-space representation that is obtained from the corresponding shear wave displacements are shown in FIGS. 1, 2 and 3, respectively. The advantages of the k-space estimation approach are that the implementation is easy, but the downsides of the k-space approach are that the errors in the estimates of the shear speed $c_s$ and shear wave attenuation can be large.

Figure 4:
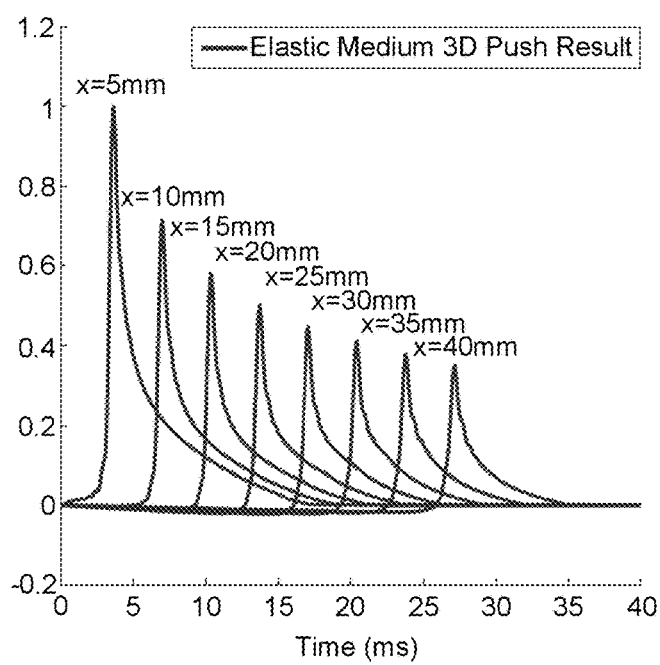
FIG. 4 is a graph depicting simulated shear displacement waveforms in an elastic medium.
Figure 5:
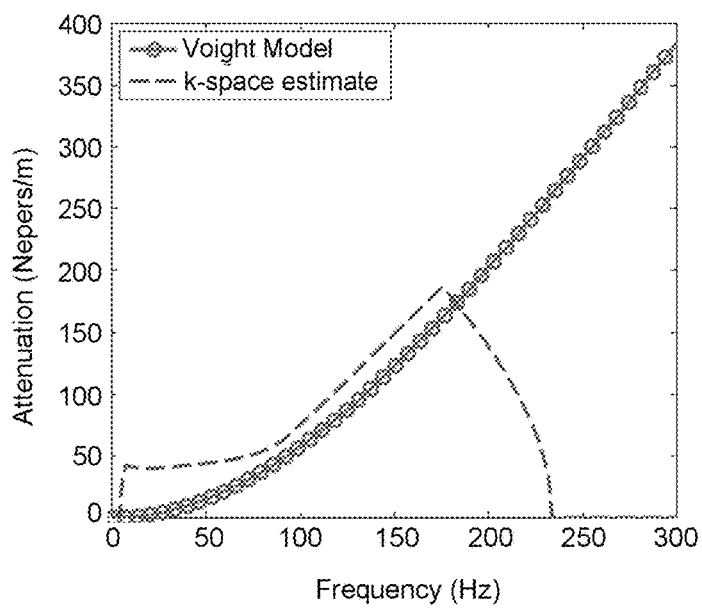
FIG. 5 is a graph showing the expected attenuation as a function of frequency predicted by the Voigt model and the estimated shear attenuation predicted by the standard k-space approach.
Figure 6:
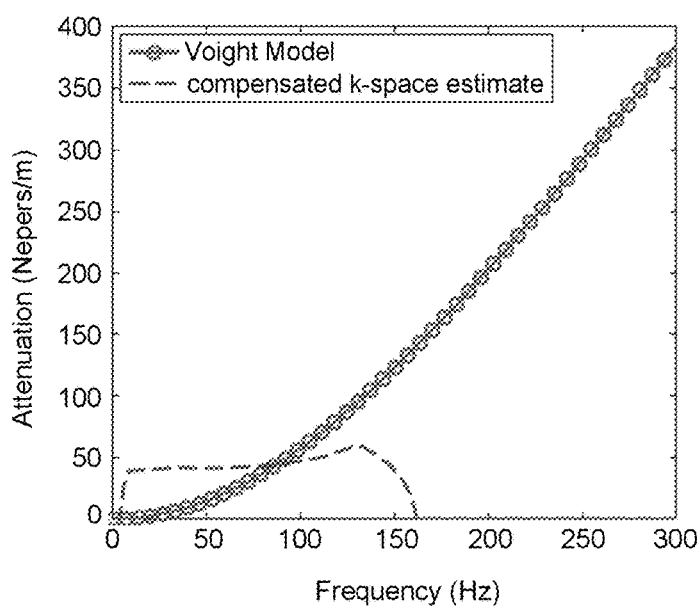
FIG. 6 is a graph showing the estimated shear attenuation predicted by a modified k-space approach that compensates for the amplitude reduction.

A critical deficiency in the k-space parameter estimation approach is an important obstacle to effective imaging of the shear viscosity $\eta_s$ with ultrasound. The source of the problem is that present implementations of the k-space model completely ignore the dispersive effects of shear wave diffraction, which causes significant errors in estimates of the shear viscosity $\eta_s$. Diffraction effects in full 3D simulations of shear waves generated by an acoustic radiation force in a purely elastic (lossless) medium include amplitude reduction (attenuation) and temporal spreading (dispersion) of the wavefront, as shown in FIG. 4. Interestingly, FIG. 4 provides an example of anomalous dispersion (i.e., reduced spreading with increasing propagation distance), and any method that fails to take diffraction effects into account will overestimate the attenuation and the dispersion while incorrectly representing the range of change (the slope) of these two quantities. FIG. 5 shows the expected attenuation as a function of frequency predicted by the Voigt model (red line with circles) for the simulated shear wave displacements shown in FIG. 2 and the estimated shear attenuation predicted by the standard k-space approach (dashed green line). FIG. 6 shows the estimated shear attenuation predicted by a modified k-space approach that compensates for the amplitude reduction (but not the temporal spreading) with an approximate $1/\sqrt{r}$ cylindrical wave model (dashed green line). These attenuation estimates should track the Voigt model across all frequencies, the shear attenuation should not decrease as a function of frequency starting at 175 Hz or 130 Hz, respectively, and the attenuation should not equal zero above 340 Hz and 160 Hz, respectively. Thus, neither k-space method yields effective shear wave attenuation estimates in this example, and the k-space method is only applicable over a relatively narrow frequency range.

To solve the shear viscosity estimation problem, it is proposed to decouple the effects of shear wave diffraction and viscosity in the time-domain. Unlike previous approaches, the proposed approach will simultaneously compensate for both the attenuative and the dispersive effects of shear wave diffraction on the estimates of shear viscosity. In an example embodiment, the proposed approach is derived from the following approximate time-domain Green's function for a shear wave propagating in a viscoelastic medium, $$g(x, t) = \frac{\overbrace{\frac{c_s\sqrt{\rho c_s}}{4\pi r \sqrt{2\pi \eta_s r}} e^{-\rho c_s^2 \left(t - \frac{r}{c_s}\right)^2 / (2\eta_s r)}}^{\text{diffraction, attenuation, and dispersion}}}{4\pi r \sqrt{2\pi \eta_s r}} = \underbrace{\frac{\delta(t - r/c_s)}{4\pi r}}_{\text{diffraction}} *_t \underbrace{\frac{c_s\sqrt{\rho c_s}}{\sqrt{2\pi \eta_s r}}}_{\text{attenuation (as a function of r)}} \underbrace{e^{-\rho c_s^3 t^2/(2\eta_s r)}}_{\text{dispersion}} \quad (3)$$

where $\rho$ is the density, $c_s$ is the shear speed, r is the distance, t is the time, $\delta(.)$ indicates the Dirac delta function, and $*_t$ indicates convolution in time. To decouple the effects of the diffraction and shear velocity, equation (3) is written as a time-domain convolution between a diffraction term and a Gaussian function that represents the effects of attenuation and dispersion through the two terms that follow the temporal convolution operation $*_t$. In equation (3), the diffraction term is independent of the shear viscosity $\eta_s$, but the Gaussian function depends on both the shear wave speed and the shear viscosity. It is envisioned that frequency-domain methods that similarly decouple the effects of shear wave diffraction and viscosity can also be developed for this purpose, and these also fall within the scope of this disclosure.

Equation (3) also motivates the framework for the proposed shear viscosity estimation approach, where the insight is to approximate a full 3D shear wave field generated in a viscoelastic (lossy) medium by a realistic 3D radiation force as the time-domain convolution between a) a full 3D shear wave field generated in an elastic (lossless) medium by a realistic 3D radiation force input and b) a Gaussian function that describes the attenuation and dispersion due to shear viscosity. This approach is preferred because repeated realistic 3D simulations of shear waves generated by an acoustic radiation force in a viscoelastic tissue model are much too time-consuming for shear wave parameter estimation. To validate the proposed model, the shear displacements in an elastic medium from FIG. 4 are convolved with the Gaussian function in equation (3), where the realistic 'push' beam that provides the acoustic radiation force is depicted in FIG. 1. In this calculation, the Gaussian function is recomputed at different distances r to account for the increase in attenuation and dispersion produced by the shear viscosity $\eta_s$ as a function of distance.

Figure 7:
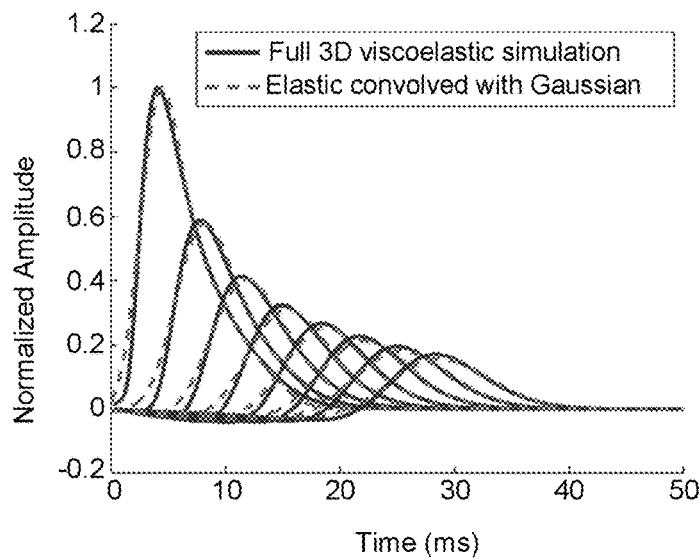
FIG. 7 is a graph showing the proposed convolution results in relation to the full 3D simulation of the shear displacement in a viscoelastic medium.

FIG. 7 compares the result of this time-domain convolution to the full 3D simulation of the shear displacements in a viscoelastic medium shown in FIG. 2, and the waveforms are very similar. This suggests that given: a) a set of simulated or measured shear wave displacements in a viscoelastic (lossy) medium and b) an effective model for the shear wave displacements generated by the same acoustic radiation force in an elastic (lossless) medium, then the shear viscosity $\eta_s$ can be estimated through deconvolution or optimization.

Figure 8:
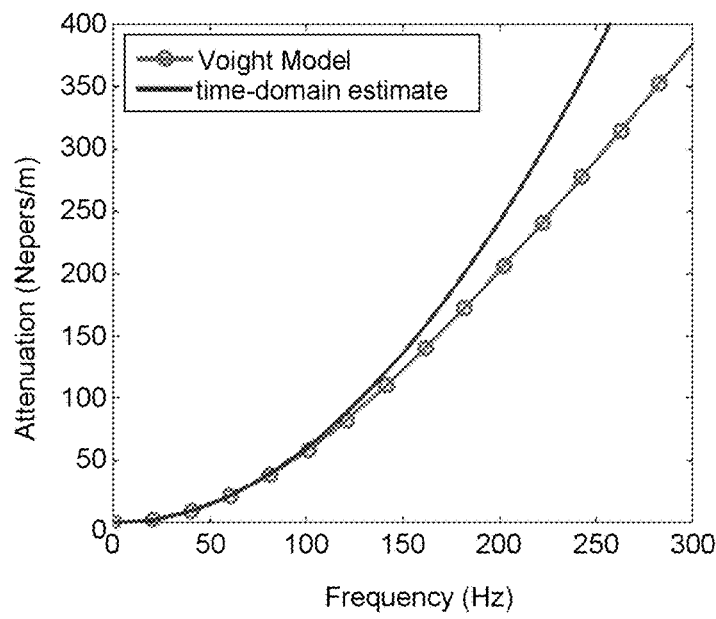
FIG. 8 is a graph showing an estimation of attenuation with the proposed approach in comparison to the Voigt model.

A preliminary evaluation of the proposed shear viscosity estimation approach is shown in FIG. 8, where $\eta_s$ is quickly estimated (in a fraction of a second) using an optimization program in MATLAB applied to the sequence of shear displacements shown in FIGS. 2 and 4 for viscoelastic and elastic media, respectively. FIG. 8 demonstrates close agreement between the frequency dependence of the attenuation that is expected for the Voigt model and the frequency dependence of the attenuation for the estimated value of $\eta_s$. This preliminary result suggests that the proposed estimation approach (FIG. 8) is much more effective for shear viscosity estimates than the uncompensated or the compensated k-space estimation approach (FIGS. 5 and 6).

Figure 9:
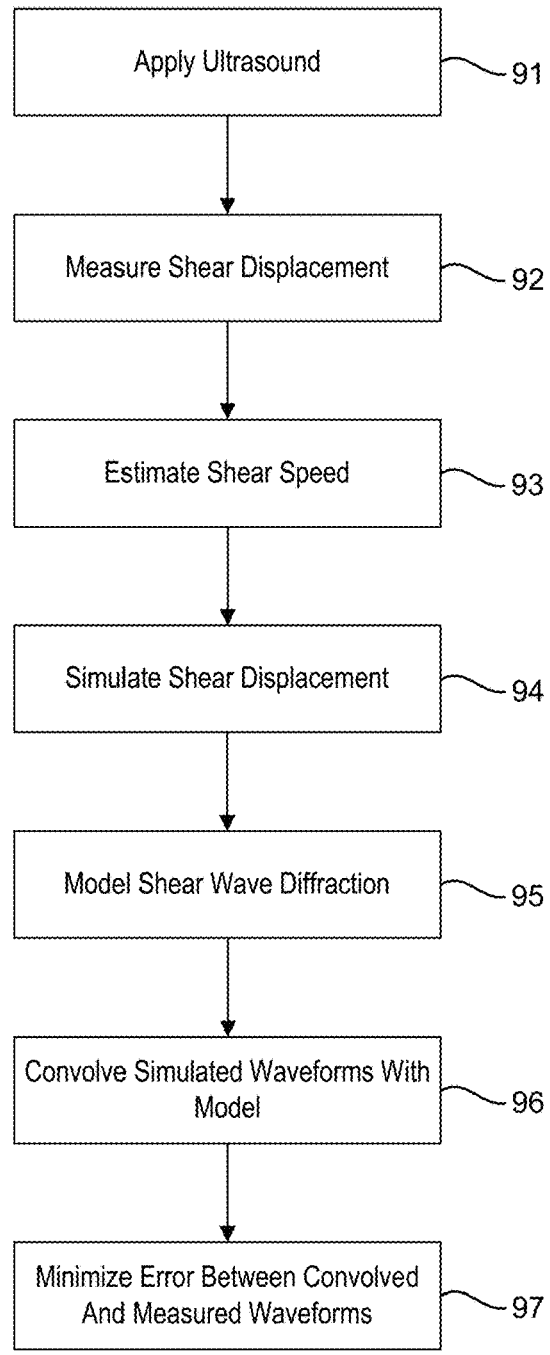
FIG. 9 is a flowchart depicting the proposed method for estimating shear viscosity for an object.

FIG. 9 provides an overview of the proposed method for estimating shear viscosity. Shear waves are generated at 91 by applying ultrasound waves to an object, such as a liver, kidney or other types of soft tissue targets. More specifically, shear waves are generated by an applied acoustic radiation force. Shear wave data representing motion of the shear wave (e.g., displacement, velocity, acceleration, etc.) can be collected and/or measured at 92 using an image transducer of the ultrasound imaging system. It is understood that shear wave data is derived from pulse-echo data captured by an imaging transducer of the ultrasound imaging system. An example of an ultrasound imaging system which may be used to implement the proposed method is the Verasonics Vantage ultrasound system although other types of commercially available ultrasound imaging systems are suitable as well.

Shear wave speed can be estimated at 93 from the measured shear wave waveforms. In one embodiment, the shear speed can be estimated using the k-space method. Briefly, the k-space approach takes a sequence of shear wave displacement or velocity waveforms collected along a line at regular intervals (the red dots in FIG. 1), forms a matrix out of these time domain waveforms, and then computes the 2D FFT (fast Fourier transform) of this matrix. From this result, the k-space estimation approach determines the shear speed $c_s$ in a lossless medium from the relation $k=\omega/c_s$. Other techniques for estimating shear speed also fall within the scope of this disclosure.

Next, a plurality of simulated shear displacement waveforms in an elastic medium are generated at 94, such that each simulated waveform corresponds to a different shear speed in a range of shear speed values. In an example embodiment, the FOCUS ultrasound simulation tool (http://www.egr.msu.edu/~fultras-web) is used to simulate the intensity field for a realistic ultrasound transducer array model. The FOCUS ultrasound simulation tool quickly and accurately simulates 3D pressure distributions to represent an acoustic radiation force. The simulated 3D acoustic radiation force displacement then serves the input for full 3D simulations of shear waves generated in an elastic medium. In the example embodiment, Green's function calculations are used to generate the simulated shear displacement waveforms. In other embodiments, a finite difference method, a finite element method, a pseudo-spectral method, or other types of numerical methods can be used.

In the example embodiment, the shear displacement waveforms are calculated for 1 kPa≤μ≤40 kPa which is the range of shear elasticities encountered in soft tissue. An increment of 0.1 m/s across the entire range of shear speed values will suffice for shear velocity estimates. For a specific transducer configuration, a plurality of shear wave displacement waveforms are generated at different shear speed values in an elastic (lossless) medium. Other shear displacement waveforms can be generated as needed for different ultrasound transducer geometries, for different material properties and for different array focusing strategies. To expedite computations, full 3D shear displacement simulations are performed in advance and the displacement waveforms are stored in a data store for later use. It is also envisioned that precalculated shear motion simulations in viscoelastic media can also be applied within this same framework and that these also fall within the scope of this disclosure.

Attenuation and dispersion effects of shear wave diffraction are modeled at 95 with a mathematical function which includes a variable indicative of shear viscosity. In the example embodiment, a Gaussian function is used to model the effects of attenuation and dispersion. Specifically, the following Gaussian function is used:

$$\frac{c_s\sqrt{\rho c_s}}{\sqrt{2\pi\eta_s r}} e^{-\frac{\rho c_s^3 t^2}{(2\eta_s r)}}$$

It is envisioned that other types of mathematical functions, such as stable probability distribution functions, can be similarly applied to model the effects of power law attenuation and dispersion in viscoelastic media, and that these also fall within the scope of this disclosure.

Each of the simulated shear displacement waveforms are then convolved at 96 with the mathematical function, thereby yielding a plurality of convolved shear displacement waveforms. Lastly, shear viscosity is estimated at 97 by minimizing the error between the measured shear displacement waveform and the plurality of convolved shear displacement waveforms. In one embodiment, the difference between the waveforms is minimized simultaneously at several locations along a line to obtain a single estimate for shear viscosity. For example, the L2 norm (or some other error metric) between the two waveforms is calculated and the value of the shear viscosity that minimizes the error is determined through an optimization procedure, such as exhaustive search, steepest descent, Newton's method, etc. Other techniques for minimizing the error between the measured waveform and the simulated waveforms are also contemplated by this disclosure.

Figure 10:
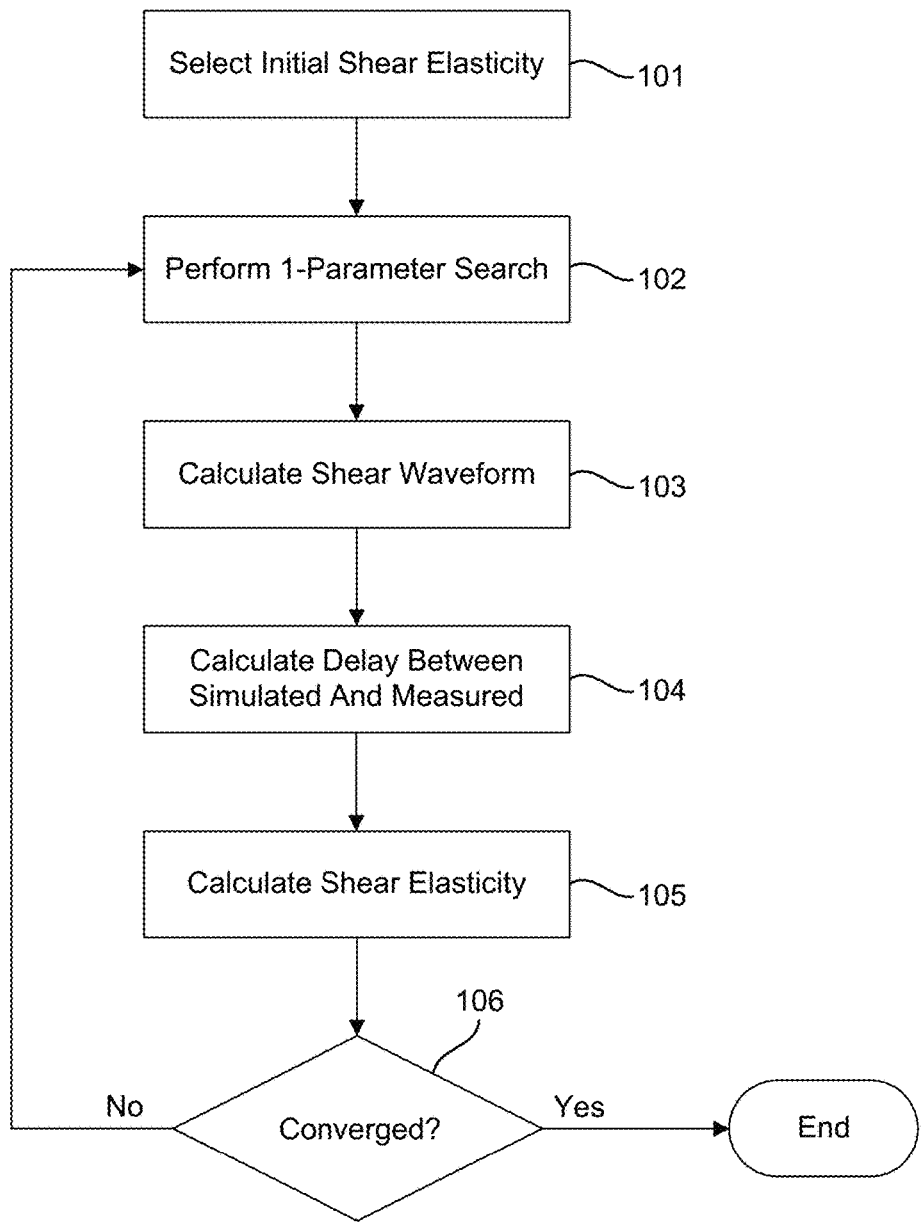
FIG. 10 is a flowchart depicting an iterative approach for estimating shear elasticity.

In another aspect of this disclosure, the method may be extended to refine the estimates for shear speed and/or shear viscosity. For example, in order to converge to the correct shear elasticity faster, an iterative approach could be employed. One iterative approach is further described in relation to FIG. 10. First, an initial value for shear elasticity is selected at 101. A 1-parameter search of shear viscosity is performed at 102, for example using the technique described above. The 1-parameter search in turn yields an estimate for shear viscosity.

Next, the shear waveform is calculated at 103 with the initial value for shear elasticity and the newly estimated shear viscosity. A time-delay is calculated at 104 between the calculated (or simulated) waveform and the measured waveform. In one example, the time delay may be calculated using a cross-correlation method. Using the time delay, an updated estimate for shear viscosity is calculated at 105. The updated estimate for shear viscosity is evaluated at 106. If an optimal value has not been reached, process is repeated using the updated estimate for the shear viscosity. Once an optimal value has been reached, the process ends.

In an alternative embodiment, the shear elasticity and the shear viscosity can be estimated sequentially, i.e., by varying the shear elasticity to minimize the error while holding the shear viscosity fixed, then by varying the shear viscosity to minimize the error while holding the shear elasticity fixed, and then repeating each of these steps a certain number of times and/or until satisfactory convergence is achieved. Essentially, this approach performs a 1D optimization on one variable, followed by a 1D optimization on the other variable, and then these optimizations are repeated as needed. For the individual 1D parameter updates, any number of optimization methods can be used, including but not limited to exhaustive search, steepest descent, Newton's method, conjugate gradient, etc.

For these iterative approaches, two examples of stopping criteria that determine when the optimal values for the shear speed (shear elasticity) and shear viscosity (shear attenuation and dispersion) are found. One is that after several iterations the averaged waveform difference reaches a static value and the changing of the waveform difference value between two iterations is small. Another is that after several iterations the estimated shear elasticity reaches a static value and he changing of the estimated shear elasticity value between the two iterations is small. Either or both of these criteria can be used for these calculations. The calculation can also be terminated if a certain number of iterations is reached, and any number of other criteria can also be applied to indicate the convergence of the estimate.

In other embodiments, the shear elasticity and the shear viscosity can be estimated simultaneously. In other words, the estimates of both parameters can be updated in a single step, also using exhaustive search, Newton's method, gradient descent, conjugate gradient, or any other optimization method. The main advantage of the 1D optimization described above is the simplicity of the implementation, where a small number of updates for each parameter is expected to yield sufficiently accurate estimates for many applications. On the other hand, the 2D optimization that updates both parameters simultaneously is expected to converge to the global minimum of the error function much more quickly and thereby achieve a better estimate for the shear elasticity and the shear viscosity in less time.

Figure 11:
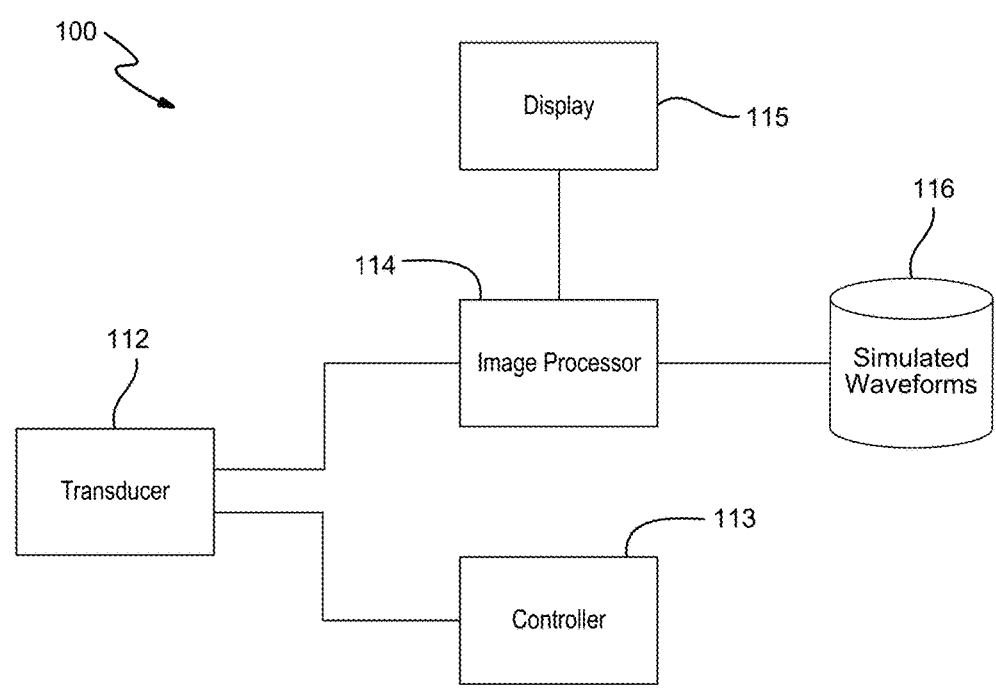
FIG. 11 is a block diagram of an example ultrasound system.

An example ultrasound system for implementing the method described above is shown in FIG. 11. The ultrasound system 100 includes a transducer 112, a controller 113, an image processor 114 and an output device 115, such as a display. The transducer 112 is used to generate a shear wave by applying ultrasound waves to the object under interrogation. Additionally, the transducer 112 is configured to collect pulse-echo data for the shear wave propagating through the object. Shear wave displacements can then be derived from the pulse-echo data. For example, the image processor 114 can use radiofrequency (RF) or in-phase/quadrature (IQ) data to estimate motion from multiple pulse-echo recordings taken at a given spatial location. The image processor 114 could use normalized cross-correlation algorithms on RF data or autocorrelation algorithms on IQ data to derive shear wave displacement. Other algorithms can also be employed by those knowledgeable in the field. The controller 112 administers the measurement process and otherwise controls the operation of the system.

From the shear wave displacement waveforms, the image processor 114 determines the shear viscosity by implementing the image processing steps described above in relation to FIG. 9. As noted above, simulated shear displacement waveforms may be computed in advance and stored in 106 (e.g., in non-transitory computer memory). Computation of the simulated shear displacement waveforms may also be computed by the image processor 114 or another computing device located remotely from the ultrasound system 100.

Images of the shear viscosity can be generated by the ultrasound system 100 based on the methods described above. As applied to full 3D simulations of the shear displacement generated by an acoustic radiation force, the shear wave speed imaging approach for a single 'push' beam is as follows: 1) collect the shear wave displacement waveforms evaluated at a single depth and 'stack' these in a matrix where one axis represents time and the other represents the spatial coordinate; 2) apply a directional filter to separate the left to right propagating shear waves from the right to left propagating shear waves; 3) calculate the time delay as a function of space by, for example, cross-correlating pairs of nearby waveforms, then determining the time delay from the point where the cross-correlation reaches a maximum; 4) divide the distances between these pairs of points by the computed time delays to obtain the shear wave speed estimates for left to right and right to left propagating shear waves; 5) average the results obtained from right to left and left to right propagating shear waves to obtain the final shear wave speed estimate as a function of the lateral coordinate; and 6) repeat this procedure for each axial distance and for multiple 'push' beams, as appropriate.

To obtain shear viscosity images, several additional steps are required. Specifically, the 3D acoustic radiation force 'push' is calculated in advance, and the 3D shear wave displacement for several different values of the shear elasticity is calculated and stored for an elastic medium with shear viscosity equal to zero.

For each point in space, the shear wave speed value is calculated as described in steps 1-6 above, and the precomputed elastic shear displacement waveforms with the shear wave speed closest to the calculated value for the shear speed are used in the following steps. That is, 7) the shear displacement waveform that was precalculated for an elastic medium with the shear wave speed closest to the estimated shear speed obtained from steps 1-6 is convolved with a Gaussian function, 8) the resulting waveform is subtracted from the output of a directional filter that was applied to the measured shear displacement waveform in step 2 above, 9) the error between these two waveforms is calculated using the L2 norm or some other error metric, and 10) the value of the shear viscosity that minimizes the error is determined through an optimization procedure, such as exhaustive search, steepest descent, Newton's method, etc. This procedure is repeated at each point in space to form an image of the shear viscosity. Images for shear viscosity can then be displayed on a display or otherwise output on a tangible medium by the ultrasound system 100. Given estimates for shear viscosity, it is also contemplated that images can be generated and displayed for shear wave attenuation, dispersion and moduli.

To further refine the estimate of the shear elasticity (shear speed), the value of the shear viscosity obtained in step 10 can then be fixed, and then the next steps are: 11) for each of the precalculated elastic shear displacement waveforms, the Gaussian function can be convolved with each of these, 12) the error is then computed for each of these (or a representative subset of these), and then 13) the value of the shear speed/shear elasticity that minimizes the error is selected for that point in space. These steps can be repeated as needed to further improve the estimates of the shear elasticity (shear wave speed) and shear viscosity (shear wave attenuation and dispersion).

As described previously, these steps can also be combined so that the shear elasticity (shear wave speed) and shear viscosity (shear wave attenuation and dispersion) are updated simultaneously through a 2D optimization procedure (as opposed to sequentially with repeated 1D optimizations, as described in steps 1-13 above).

In other embodiments, one can calculate waveforms for different combinations of the shear elasticity (shear wave speed) and shear viscosity (shear wave attenuation and dispersion) in advance, store the resulting shear displacement waveforms, and then estimate the values of the shear elasticity (shear wave speed) and shear viscosity (shear wave attenuation and dispersion) using these stored waveforms instead. Other embodiments can also replace the precalculated waveforms with functions or other numerical calculations that are performed quickly during the estimation procedure to represent the effects of diffraction and/or attenuation and dispersion.

As an alternative to precalculating the shear wave displacements in an elastic medium, storing these, and using these in the estimation procedure above, one can instead use an analytical approximation to represent the effect of diffraction on the shear wave and achieve a significant improvement in the estimated values that are obtained with the k-space or time-of-flight correlation models, which are both inherently plane wave models. For example, the time-domain Green's function for a cylindrical wave is $$g(r, t) = \frac{H\left(t - \frac{r}{c_s}\right)}{2\pi\sqrt{t^2 - r^2/c^2}},$$

and this expression can be used as the shear wave diffraction model. However, there is a problem with this expression for numerical calculations, namely the divide by zero problem at t=r/c. This problem is eliminated by analytically convolving the time-domain Green's function for a cylindrical wave with another analytical expression that can, for example, represent the duration of the acoustic radiation force 'push.' A 'rect' function is an example of one such analytical function that can be convolved with the Green's function for a cylindrical wave, yielding $$g(r,t) = \frac{1}{2\pi}\ln\left(\frac{\sqrt{t^2 - \frac{r^2}{c_s^2}} + t}{\frac{r}{c_s}}\right)\left[H\left(t - \frac{r}{c_s}\right) - H\left(t - \frac{r}{c_s} - W\right)\right] +$$

$$\frac{1}{2\pi}\ln\left(\frac{\sqrt{t^2 - r^2/c_s^2} + t}{\sqrt{(t-W)^2 - \frac{r^2}{c_s^2}} + (t-W)}\right)H\left(t - \frac{r}{c_s} - W\right),$$

and then the above expression can be used as the diffraction term in Eq. 3. Although sequential 1D optimizations can then be used in the estimation of shear elasticity (shear speed) and shear viscosity (shear attenuation/dispersion), 2D optimizations are expected to achieve better results in less time with these functions or with other rapid numerical calculations that provide similar information.

This approach can also be extended to the frequency domain, where the equation given in the preceding paragraph or a similar expression can be evaluated in the time domain, then analytically or numerically Fourier transformed (using FFTs, DFTs, etc.), and then the Gaussian function (or other probability distribution function) can likewise be analytically or numerically Fourier transformed. The product can be evaluated in the frequency domain, and then a similar expression for the error can be calculated in the frequency domain, or the result can be analytically or numerically inverse transformed and then the error can be evaluated in the time domain.

Another extension of this approach in the frequency domain involves multiplying the frequency domain Green's function for a cylindrical wave, $$g(r,\omega) = \frac{j}{4}H_0^{(1)}(\omega r/c_s),$$

or the far field approximation to the frequency domain Green's function for a cylindrical wave, $$g(r,\omega) \approx \frac{j}{4}\sqrt{\frac{2c_s}{\pi\omega r}}e^{j\left(\frac{\omega r}{c_s} + \frac{\pi}{4}\right)},$$

by the Fourier transform of a Gaussian function (which is also a Gaussian function) or by the Fourier transform of a stable distribution or some other function and then multiplying these in the frequency domain. This product can also be multiplied by another analytical function that represents the Fourier transform of the duration and/or envelope of the acoustic radiation force push. Although the DC component of the result will be infinite, the other frequency components will still be finite, and the parameter estimation can be performed just with the finite frequency components.

This approach and all of the other approaches described herein are applicable to measured shear wave displacements, shear wave velocities, or any other form of shear motion.

An example of the shear viscosity imaging procedure, including the intermediate results obtained from each step, is given here. First, the 3D pressure field generated by the ultrasound transducer in a soft tissue model is computed, then the 3D intensity distribution is calculated from the 3D pressure field, and finally the 3D acoustic radiation force 'push' is obtained from $$f(r,t) = \frac{2\alpha I(r,t)}{c_P}.$$

Although the source can be any single transducer element or array, focused or unfocused, in this example the results are obtained with a simulated linear ultrasound imaging array with a focused beam. The array used in these simulations is a simulated Phillips L7-4 128-element linear array. The elements in this array are 0.283 mm wide, 7 mm high, the kerf is 0.025 mm wide, the elevation focus is at 25 mm, and the excitation frequency is 4.09 MHz. The electronic focus for these simulations is located 25 mm from the array and is generated by 40 contiguous transducer elements. The attenuation in the simulation model is 0.5 dB/cm/MHz, and the compressional wave speed is 1500 m/s.

Figure 12:
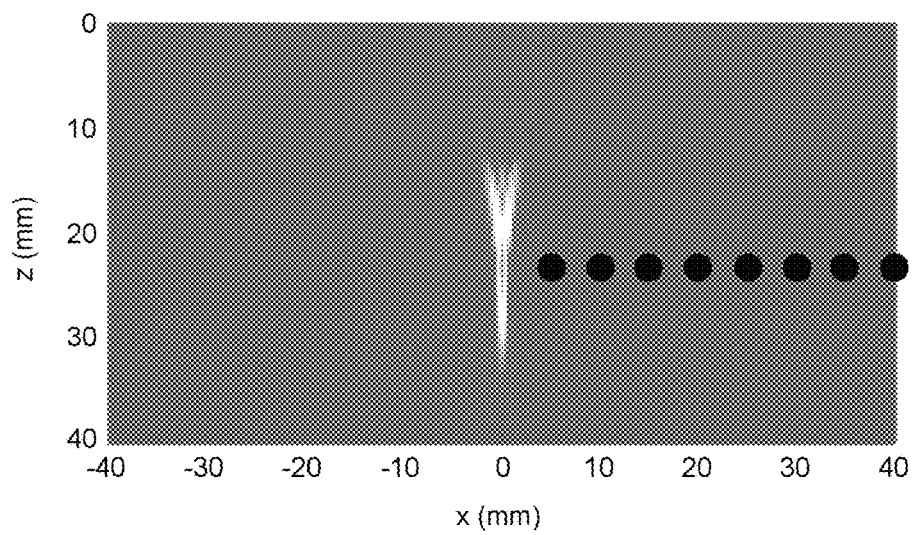
FIG. 12 is an image of a simulated pressure field generated by 40 contiguous elements in a 128-element linear array.

The 3D pressure field is calculated in FOCUS (http://www.egr.msu.edu/~fultras-web) with the fast nearfield method combined with the angular spectrum approach. A 2D cross-section of the calculated pressure field is shown in FIG. 12, which also contains several red dots that indicate the locations where the shear wave displacements are calculated in the figures shown below.

The acoustic radiation force f(r,t) is then modeled as f(r,t)=f(r)w(t), where f(r) is the spatial distribution of the acoustic radiation force calculated with the fast nearfield method combined with the angular spectrum approach, and w(t) is a window function in time that describes the time duration of the applied acoustic radiation force. In this example, the window function is given by w(t)=rect[(t−T/2)/T], where rect(•) is the 'rect' or boxcar function, and T is the duration of the acoustic radiation force 'push.'

Figure 13:
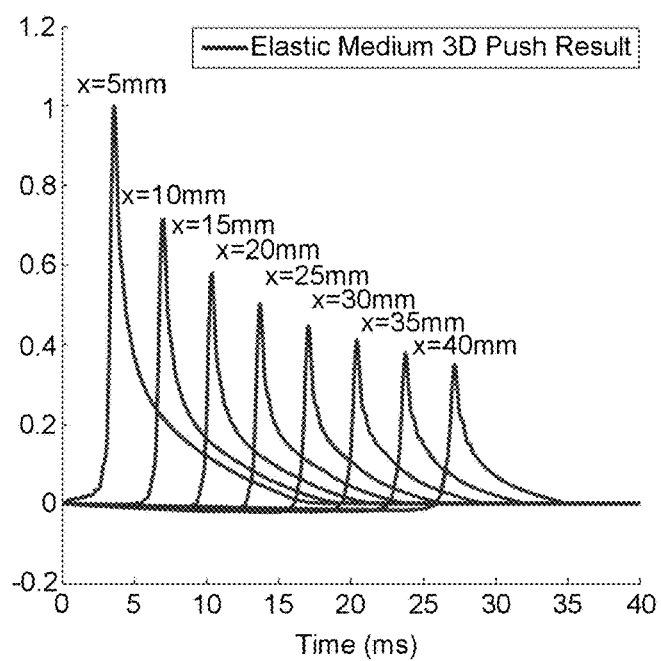
FIG. 13 is a graph showing simulated shear displacements in an elastic medium evaluated at z=22.9 mm with W=200 μs, $c_s$=1.48 m/s, and ρ=1000 kg/m³, where these shear displacements are generated by the 'push' beam in FIG. 12.
Figure 14A:
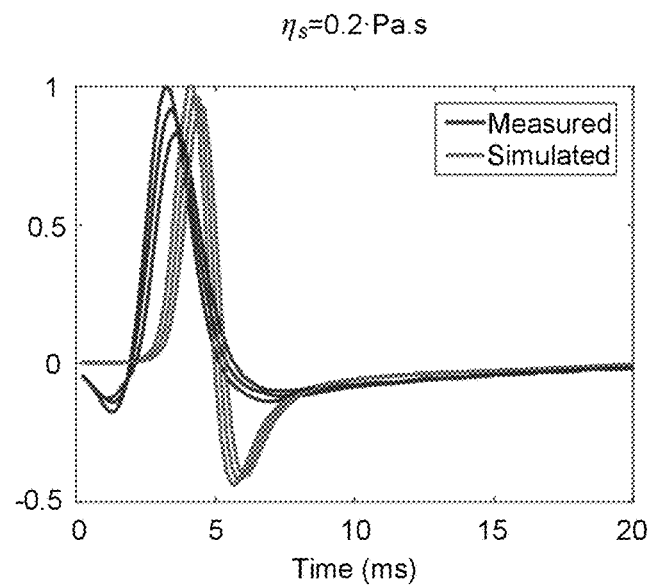
FIGS. 14A and 14D are graphs showing comparisons between measured and simulated shear displacement waveforms, where the measured waveforms were collected from a viscoelastic shear wave phantom with a Phillips L7-4 128-element linear array connected to a Verasonics ultrasound scanner.
Figure 14B:
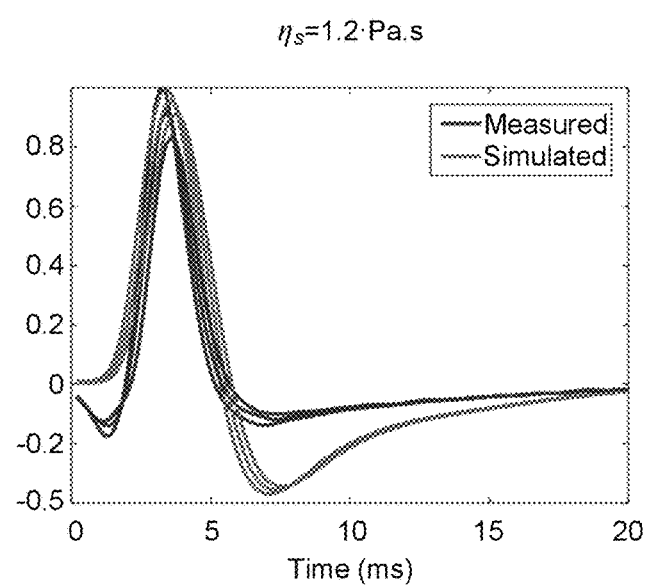
Figure 14C:
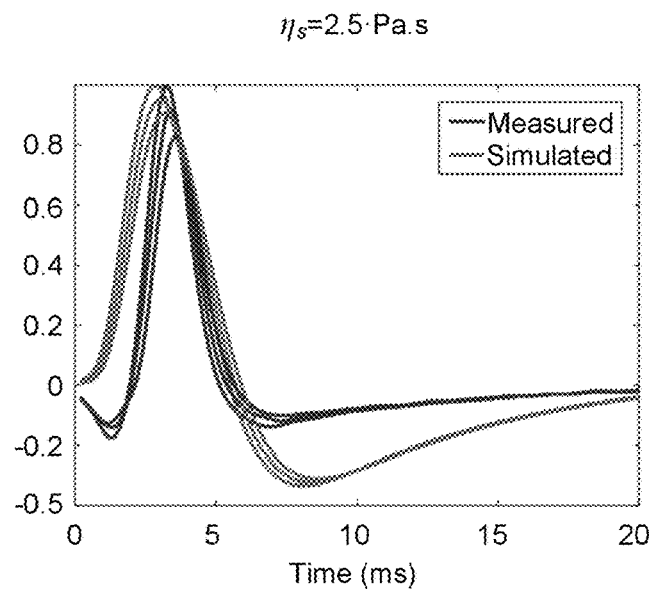
Figure 14D:
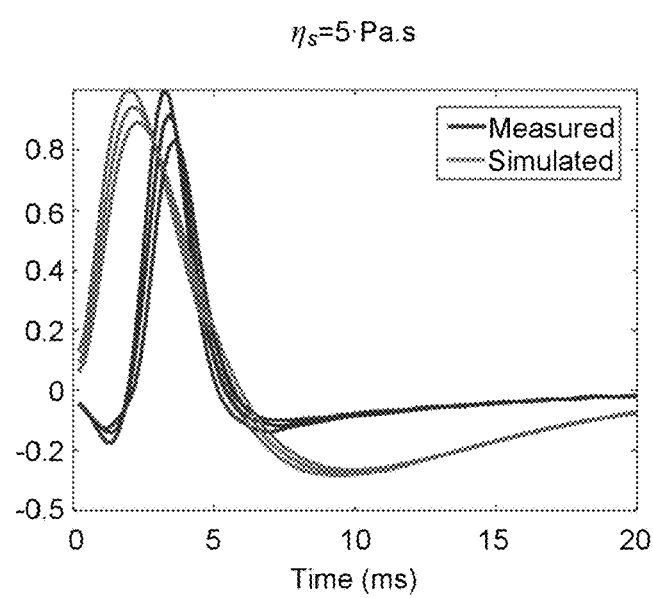

The acoustic radiation force 'push' with this time-dependence then provides the input to the elastodynamic equation of motion (i.e., Navier's equation with no viscous loss), which is given by $$\left[\lambda + \mu + \frac{\partial}{\partial_t}\right]\nabla\nabla \cdot u + \left(\mu + \frac{\partial}{\partial_t}\right)\nabla^2 u + \rho f = \rho\ddot{u},$$

where $\lambda$ and $\mu$ are the Lamé constants, respectively, p is the density, $c_p=\sqrt{(\lambda+2\mu)/\rho}$ and $c_s=\sqrt{\mu/\rho}$ are the compressional and shear speeds, respectively, u is the vector displacement, and f is the body force. The 3D shear displacements or shear velocities as a function of time are calculated for several different values of $\mu$ within an entire 2D image plane, i.e., for 19 mm to 19 mm in x and for 0 mm to 96 mm in z. Examples of shear displacement waveforms calculated at the 8 red dots shown in FIG. 12 are shown in FIG. 13 for a single value of the shear elasticity $\mu$ with W=200 μs, $c_s$=1.48 m/s, and $\rho$=1000 kg/m³. For these calculations, the 3D shear displacements or shear velocities are calculated using a Green's function approach (such as that described by Bercoff, although other numerical methods such as finite differences, FEM, etc. will be equally effective for this step) for all values of $\mu$ that are within the range encountered in soft tissue. For the precalculated shear displacement waveforms calculated in this example, the maximum value of $c_s$ is 3.5 m/s, the minimum value of $c_s$ is 1.5 m/s, and the increment is 0.1 m/s, where the shear displacements as a function of time is calculated in a 2D spatial grid for this entire range of values for $c_s$ and stored for use in the subsequent steps.

At each point in space, the precomputed shear displacement waveforms with the value of $\mu$ that is closest to the initial estimate obtained from steps 1-6 noted above is extracted from memory. Then, in step 7, the shear displacement waveform is convolved with the Gaussian function $$h(r, t) = \frac{c_s \sqrt{\rho c_s}}{\sqrt{2\pi \eta_s r}} e^{-\frac{\rho c_s^3 t^2}{(2\eta_s r)}}$$

for several different values of the shear viscosity. For these calculations, the error is evaluated using $$\frac{\|v_m - v_s\|}{\|v_s\|},$$

where the measured shear displacement waveform is indicated by $v_m$, the simulated shear waveform (which is the precomputed shear displacement waveforms in an elastic medium convolved with a Gaussian function) is indicated by $v_s$, and $\|.\|$ is the L2 norm. The term in the denominator normalizes the result, which can also be normalized with $\|v_m\|$ in the denominator. Before calculating the difference in the above expression, both the measured and simulated shear displacement waveforms are also normalized so that the peak value of each is equal to '1' to remove any differences in the waveforms due to scaling. Steps 8 and 9 thus calculate the difference between the measured and simulated waveforms and then evaluate the norm of that difference, respectively.

In this example, the value of $\eta_s$ is optimized in step 10 through an exhaustive search for the point located at (x=15 mm, z=30 mm). The minimum value of $\eta_s$ used in this optimization is 0.1 Pa·s, the maximum value is 6 Pa·s, and the increment is 0.1 Pa·s. FIGS. 14A-14D show measured and simulated shear displacement waveforms evaluated at 3 adjacent points centered at (x=15 mm, z=30 mm), where the blue line indicates the measured shear displacements obtained from a viscoelastic shear wave phantom, and the red line indicates the waveforms obtained when the precomputed shear displacements in an elastic medium are convolved with the Gaussian function above for four different values of $\eta_s$, namely 0.2 Pa·s, 1.2 Pa·s, 2.5 Pa·s, and 5 Pa·s. The shear wave speeds are the same in all 4 subfigures with $c_s$=1.8 m/s, so the only differences in these figures are due to changes in the value for $\eta_s$. Of these four values, $\eta_s$=1.2 Pa·s has the smallest error, which suggests that the best alignment between the measured and simulated shear displacement waveforms is achieved with this value of $\eta_s$.

This procedure is then repeated at each point in the xz plane, and then an image of $\eta_s$ is formed with the results. In the resulting images shown in this example, the minimum value of x is 19 mm, the maximum value is 19 mm, and the increment is 0.345 mm. The minimum value of z is 10 mm, the maximum value is 96 mm, and the increment is 0.345 mm.

Figure 15A:
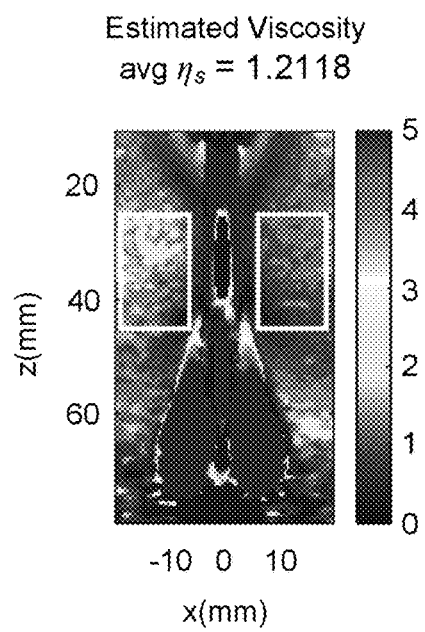
FIGS. 15A and 15B are an image of shear viscosity obtained from a viscoelastic shear wave phantom using the method described herein and an image of the waveform difference, respectively.
Figure 15B:
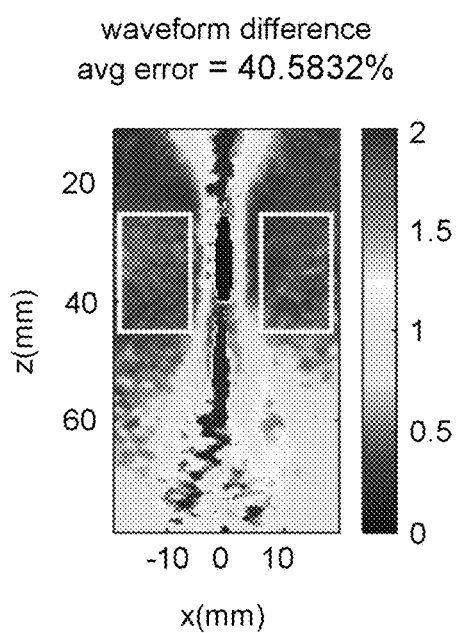

FIG. 15A shows the resulting shear viscosity image. Two square white boxes are defined on either side of the focal peak, and then the average shear viscosity is evaluated within these boxes. The box spans from ±6 mm to ±18 mm in the x direction, and from 25 mm to 45 mm in the z direction. The average value of the shear viscosity within these boxes is 1.21 Pa·s. FIG. 15B shows that the errors are generally smaller on either side of the focal peak, where the white boxes therefore cover a large portion of the region where the error is smallest and the estimate of the shear viscosity is expected to yield the most accurate results.

One then uses the estimate for the shear viscosity to update the initial shear speed estimate, which implicitly assumes that the shear viscosity is equal to zero. To update the value for the shear speed at each point in space, the Gaussian function is calculated with the value of the shear viscosity (e.g., the average value of the shear viscosity in the two white boxes in FIG. 15A). Then, the precomputed shear displacement waveforms calculated in an elastic medium are recovered from memory, and in step 11, each of these precomputed waveforms are convolved with the Gaussian function in the time domain. For each precomputed shear displacement waveform, step 12 calculates the error as above. Then, step 13 optimizes the value of the shear speed that minimizes the error at each point in space to form an updated image of the shear speed that compensates for the value of the shear viscosity that was obtained through the previous steps. In this example, the optimal value for $c_s$ at each point in space was obtained through an exhaustive search, though any number of optimization methods can also be applied here. The resulting image is shown in FIG. 16A. For purposes of comparison, the initial shear speed image calculated with steps 1-6 is also shown for the same viscoelastic shear wave phantom. When the waveform difference errors are computed for these two values of the shear speed, the errors in the shear speeds calculated after compensating for the shear viscosity are consistently smaller by a significant amount, which indicates that the shear viscosity compensated image of the shear speed in FIG. 16B provides a much more accurate estimate.

The shear wave speed and shear viscosity images can then be refined sequentially (i.e., an improved value for $\eta_s$ can then be obtained by applying steps 7-10 to this updated value for $c_s$, followed by another refinement of $c_s$ using steps 11-13 based on the latest update for $\eta_s$), or a 2D optimization procedure can simultaneously refine the estimates for $c_s$ and $\eta_s$. The error metric is evaluated for all of the values of $c_s$ and $\eta_s$ that were considered in the previous exhaustive search optimizations described above, and the result is shown in FIG. 17. In this figure, the black 'x' indicates the value of the shear speed obtained in the viscoelastic shear wave phantom at (x,z)=(15 mm, 30 mm) after steps 1-6 are completed. This value is clearly suboptimal. The white circle indicates the optimal values of the shear speed and the shear viscosity, which are $c_s$=1.81 m/s and $\eta_s$=1.21 Pa·s. It is envisioned that a 2D optimization procedure will be very effective in determining these optimal values. However, experience thus far has also shown that completing steps 1-13 just once obtains values for of $c_s$ and $\eta_s$ that are sufficiently close to the optimal values.

The techniques described herein may be implemented in part by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for determining shear viscosity for an object under interrogation, comprising:
applying an ultrasound wave to the object;
measuring a shear wave waveform representing motion of a shear wave propagating through the object, where the shear wave is caused by the ultrasound wave applied to the object;
estimating shear wave speed from the measured shear wave waveform;
generating a plurality of simulated shear wave waveforms in an elastic medium, where each simulated shear wave waveform in the plurality of simulated shear wave waveforms corresponds to a different shear speed in a range of shear speed values;
modeling attenuation and dispersion effects of shear wave diffraction with a mathematical function, where the mathematical function includes a term indicative of shear viscosity;
convolving each of the simulated shear wave waveforms in the plurality of simulated shear wave waveforms with the mathematical function to yield a plurality of convolved shear displacement waveforms; and
estimating shear viscosity for the object by minimizing error between the measured shear wave waveform and the plurality of convolved shear displacement waveforms.

2. The method of claim 1 further comprises estimating shear wave speed from the measured shear wave waveform using a k-space method.

3. The method of claim 1 further comprises generating a plurality of simulated shear wave waveforms using Green's functions.

4. The method of claim 1 further comprises generating a plurality of simulated shear wave waveforms using one of a finite difference method, a finite element method, or a pseudo-spectral method.

5. The method of claim 1 further comprises modeling attenuation and dispersion effects of a shear wave diffraction using a Gaussian function.

6. The method of claim 1 wherein the mathematical function is defined as $$\frac{c_s\sqrt{\rho c_s}}{\sqrt{2\pi\eta_s r}} e^{-\frac{\rho c_s^3 t^2}{(2\eta_s r)}}$$

where $\rho$ is the density, $c_s$ is the shear speed, r is the distance, t is the time and $\eta_s$ is shear viscosity.

7. The method of claim 1 wherein minimizing error between the measured shear wave waveform and the plurality of convolved shear wave waveforms further comprises minimizing L2 norm simultaneously at several spatial locations.

8. The method of claim 1 further comprises generating images of shear viscosity using the estimated shear viscosity and displaying the images of shear viscosity on a display.

9. The method of claim 8 further comprises generating images of the shear viscosity by performing, at different points in space within the object, the steps of estimating the shear wave speed, generating a plurality of simulated shear wave waveforms, convolving each of the simulated shear wave waveforms and estimating the shear viscosity.

10. The method of claim 1 further comprises estimating shear wave speed by varying the shear viscosity while holding shear wave speed fixed.

11. The method of claim 10 further comprises estimating the shear wave speed by varying the shear viscosity while holding shear wave speed fixed, then estimating the shear speed by varying shear wave speed while holding shear viscosity fixed and repeating these steps until a convergence criterion is met.

12. The method of claim 10 wherein estimating shear speed further comprises
generating a second plurality of simulated shear wave waveforms, where each simulated shear wave waveform in the second plurality of simulated shear wave waveforms corresponds to a different shear viscosity in a range of shear viscosity values;
convolving each of the simulated shear wave waveforms in the second plurality of simulated shear wave waveforms with the mathematical function to yield a second plurality of convolved shear displacement waveforms; and
estimating shear viscosity for the object by minimizing error between the measured shear wave waveform and the second plurality of convolved shear displacement waveforms.

13. The method of claim 1 wherein estimating shear viscosity further comprises estimating shear wave speed and shear viscosity simultaneously using one of an exhaustive search, Newton's method, steepest descent method, or conjugate gradient method.

14. A method for generating images of shear viscosity for an object under interrogation, comprising:
applying an ultrasound wave to the object using an imaging transducer;
measuring a shear wave waveform representing displacement of a shear wave propagating through the object, where the shear wave is caused by the ultrasound wave applied to the object and is measured using an imaging transducer;
estimating shear wave speed from the measured shear wave waveform;
modeling displacement of a shear wave with a mathematical function having at least two terms, including a first term representing diffraction of the shear wave convolved with one or more additional terms, where the one or more additional terms represents attention and dispersion of the shear wave and has a variable indicative of shear viscosity;
generating a plurality of simulated shear wave waveforms in an elastic medium, where each simulated shear wave waveform in the plurality of simulated shear wave waveforms has a different shear speed within in a range of shear speeds;
convolving each of the simulated shear wave waveforms in the plurality of simulated shear wave waveforms with the second and third terms of the mathematical function to yield a plurality of convolved shear displacement waveforms; and
estimating shear viscosity for the object by minimizing error between the measured shear wave waveform and the plurality of convolved shear displacement waveforms.

15. The method of claim 14 wherein the mathematical function is defined as $$\overline{\frac{\delta(t-r/c_s)}{4\pi r}} * t \overline{\frac{c_s\sqrt{\rho c_s}}{\sqrt{2\pi \eta_{sr}}}} e^{-\rho c_s^3 t^2/(2\eta_s r)}$$

where $\rho$ is the density, $c_s$ is the shear speed, r is the distance, t is the time and $\eta_s$ is shear viscosity.

16. The method of claim 14 wherein the one or more additional terms are modeled using a Gaussian function.

* * * * *

UNITED STATES PATENT AND TRADEMARK OFFICE
CERTIFICATE OF CORRECTION

PATENT NO. : 10,534,076 B2
APPLICATION NO. : 15/577711
DATED : January 14, 2020
INVENTOR(S) : Robert J. McGough et al.

It is certified that error appears in the above-identified patent and that said Letters Patent is hereby corrected as shown below:

In the Specification

Column 9, Line 18, "quadrature (10) data" should read --quadrature (IQ) data--.

Signed and Sealed this
Third Day of March, 2020

Andrei Iancu
*Director of the United States Patent and Trademark Office*